US00PP28311P3

(12) United States Plant Patent
Molnar et al.

(10) Patent No.: US PP28,311 P3
(45) Date of Patent: Aug. 22, 2017

(54) ***CORNUS KOUSA* TREE DESIGNATED 'RUTPINK'**

(50) Latin Name: *Cornus kousa*
Varietal Denomination: Rutpink

(71) Applicant: Rutgers, The State University of New Jersey, New Brunswick, NJ (US)

(72) Inventors: Thomas J. Molnar, East Brunswick, NJ (US); John M. Capik, Somerset, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/756,233

(22) Filed: Aug. 19, 2015

(65) Prior Publication Data

US 2017/0055409 P1 Feb. 23, 2017

(51) Int. Cl.
*A01H 5/00* (2006.01)

(52) U.S. Cl.
USPC ..... Plt./220

(58) Field of Classification Search
USPC ..... Plt./216, 220
See application file for complete search history.

*Primary Examiner* — Susan McCormick Ewoldt
(74) *Attorney, Agent, or Firm* — James A. Lucas; Driggs, Hogg, Daugherty & Del Zoppo Co., LPA

(57) ABSTRACT

A new *Cornus kousa* cultivar that is clearly distinguished by its floriferous display of showy, dark-pink floral bracts, attractive dark-green foliage, high level of winter hardiness, and tolerance of the incitants of powdery mildew.

4 Drawing Sheets

Latin name of genus and species of the plant claimed: *Cornus kousa* Buerger×Miq.
Variety denomination: Rutpink.

CROSS REFERENCE TO RELATED APLICATIONS

NONE

STATEMENT REGARDING FEDERALLY SPONSORED RESEARCH OR DEVELOPMENT

NONE

Description

Botanical designation: *Cornus kousa* Buerger ex Miq.
Variety denomination: 'Rutpink'.

BACKGROUND OF THE INVENTION

This new cultivar is the product of a long standing program of hybridization and selection of big-bracted dogwoods, in this instance the result of an open-pollination event of an unnamed pink-bracted *Cornus kousa* tree held in the germplasm collection at a New Jersey university. The purpose of the program was to develop new and superior cultivars of dogwoods expressing consistently dark-pink floral bracts that are cold hardy in New Jersey and similar climates. The seed parent of this new cultivar is a pink-bracted, unreleased breeding selection designated as K187-44 which resulted from a cross of *Cornus kousa* 'Satomi' and *C. kousa* 'Benifuji' made in 1996 by Dr. Elwin Orton. The male (pollen) parent is unknown but from a limited breeding block of improved dogwood trees existing in an isolated area. The progeny from which the plant in question was selected were analyzed for their differences and outstanding value as potential commercial cultivars.

We selected the particular seedling hereof from certain progeny grown in a cultivated area, and as a result, have in turn caused the same to be asexually reproduced by budding, grafting, and micropropagation (plant tissue culture). The reproduction and actual growth and selection of the new cultivar took place in the vicinity of New Brunswick, N.J. The claimed cultivar is stable and reproducible true-to-type in successive generations of asexual reproduction.

As will be understood from the detailed description of the invention which appears hereinafter, the new cultivar is in fact outstanding and readily identified as being such. With the foregoing in mind, the description which follows will be understood as clearly defining the new cultivar, the desirable characteristics of which are the result of such a program as has been heretofore stated.

SUMMARY OF THE INVENTION

The cultivar, designated here as 'Rutpink', originated in cultivated field #3 at a horticultural farm at said New Jersey university in New Brunswick, Middlesex County, N.J., 08901. This seedling originally resulted from an open-pollination event in 2008 of a *Cornus kousa* tree designated K187-44, which is located in Row 4, tree 39 in Field 70 at the university's research and extension farm in Adelphia, N.J.

The seedling, which became this new cultivar, germinated in February 2009, was transplanted to progressively larger containers, and was finally transplanted to the field in September 2009 at said horticulture farm in New Brunswick, N.J. Five grafts were made of this tree in March 2013 and two were subsequently field planted at the same farm in September 2014 for further observation along with the original seedling. The plant was also propagated by budding onto *C. kousa* and *C. florida* seedling rootstock in August 2013 in Belvidere, Tenn., 37306 and Boring, Oreg., 97009, and was subsequently evaluated in those regions for propagation performance, powdery mildew response, growth habit and leaf quality, and floral bract color in 2015 in TN.

The dogwood tree of the present invention is asexually propagated by grafting (usually T-budding or chip-budding but also side-veneer grafting), by softwood cuttings, or via meristem culture (plant tissue culture). It is distinguished from patented and/or commercially available cultivars of pink-bracted *Cornus kousa* or *C. florida*×*C. kousa* hybrids in the following respects:

A group of five pink-bracted *Cornus kousa* cultivars widely available in the nursery trade includes 'Satomi' (also called 'Miss Satomi not patented), 'Rosabella' (not patented), 'Rosea' (not patented), 'Schmred' (Heart Throb®, expired U.S. Plant Pat. No. 9,283), and 'Hanros' (Radiant Rose® not patented. These five cultivars are very similar to one another in terms of mature floral bract shape and color and are clearly different than 'Rutpink'. It should be noted that Trigiano et al. (2004) showed that when using molecular markers, 'Rosabella', 'Satomi', and 'Schmred' (Heart Throb®, had nearly identical fingerprints suggesting they are the same cultivar or are full-siblings of one another. The five cultivars have mature floral bracts that are ovate to obtuse in shape (Cappiello and Shadow, 2005), whereas 'Rutpink' has floral bracts that are distinctly acuminate as clearly described hereinafter. The floral bracts of 'Rutpink' are also generally larger in size than these five cultivars when measured from the tip of one opposing floral bract to the other at the time of anthesis. Further, under New Jersey conditions in late May to early June when air temperatures can reach over 85 degrees Fahrenheit (26.7 Celsius), floral bract color in full sun at the time of anthesis for the five available cultivars is generally light pink to cream color with an uneven shading (typical base color of floral bracts is 36 C and 36 D Red Group based upon The Royal Horticultural Society (R.H.S.) Colour Chart (1966) with intermittent splotches of 49 A Red Group and edges of floral bracts sometimes reaching 50 B Red Group). In contrast, the floral bracts of 'Rutpink' remain uniform in color and are generally much darker pink, with the color most closely approximated by 54 A and 54 B Red Group, with a majority of the bracts 54 B Red Group. Further, 'Rutpink' has a distinct reflective quality of the floral bracts that display a brilliant pink color on a landscape level. This is lacking in the other cultivars which, under hot New Jersey air temperature conditions, appear cream colored to very pale pink at a distance.

'Benifuji (expired U.S. Plant Pat. No. 8,676) differs from 'Rutpink' due to its smaller floral bracts at the time of anthesis, which average around 8-9 cm when measured from the tip of one opposing floral bract to the other whereas 'Rutpink' averages over 13 cm. Further, the time of anthesis of 'Benifuji' is regularly about 5-7 days later than 'Rutpink' and, under New Jersey conditions, the floral bracts of 'Benifuji' are consistently lighter pink although generally darker than the five cultivars referenced above.

'KN144-2' Rosy Teacups™ (Plant patent) differs from 'Rutpink' in the upward growth and development of its young floral bracts up until around the point of anthesis. Also, the bracts of 'KN144-2' are slightly larger and ovate in shape with a slight overlap of the basal 30% of the length of neighboring bracts, whereas 'Rutpink' has distinctly acuminate floral bracts with less than 10% overlapping of neighboring bracts at their base at anthesis. The floral bracts of 'Rutpink' are also generally a darker pink color at anthesis in New Jersey.

'Rutgan' (Stellar Pink®; expired U.S. Plant Pat. No. 7,207) is an interspecific hybrid between *Cornus florida* and *Cornus kousa*, which has smaller floral bracts than 'Rutpink' that are nearly rounded to obovate in shape with short, acute tips and tapered bases that are more overlapping. 'Rutgan' blooms around two weeks before 'Rutpink', indicative of its hybrid background, with an anthesis date between that of the earlier blooming *Cornus florida* and the later blooming (approximately 1 month) *Cornus kousa*. 'Rutgan' is also sterile, producing no mature fruit, whereas 'Rutpink' produces abundant fruit with fertile seeds.

BRIEF DESCRIPTION OF THE DRAWINGS

This new cultivar of dogwood is illustrated by the accompanying digital photographs, depicting defining characteristics of the plant by the best possible color representation using digital color photography. All color references herein are measured against said Royal Horticultural Society (R.H.S.) Colour Chart (1966). Colors are approximate as individual color depends on horticultural practices such as light level, temperature, and fertilization rate, among others.

BOTANICAL DESCRIPTION OF THE INVENTION

Figure 1:
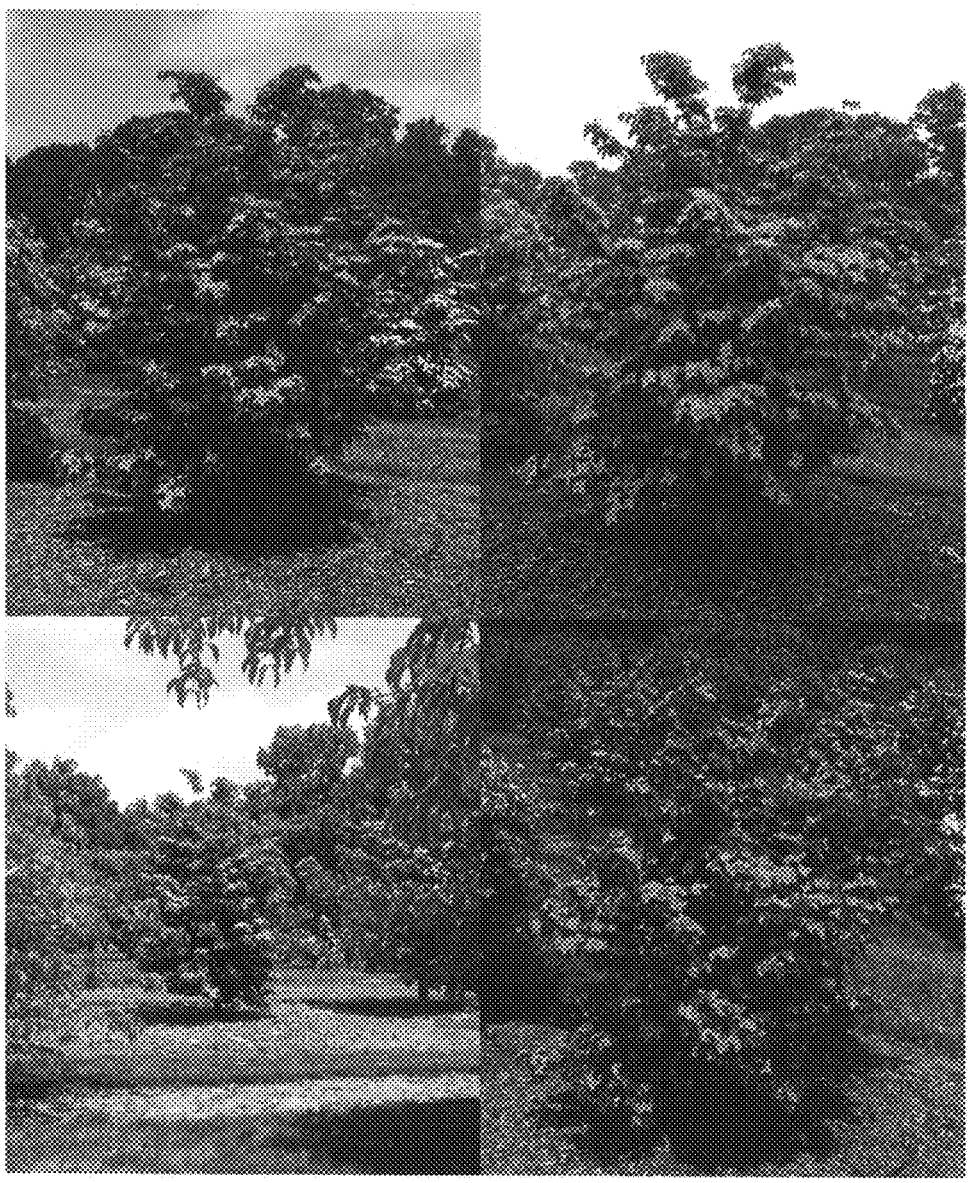
FIG. 1 shows four images of a dogwood tree of the present invention at peak floral display after 7 growing seasons. Multiple images are shown to present the different floral bract color displays depending on the level of sunshine, distance from tree, and angle of viewing. From left to right top to bottom: (A) photograph taken from ground level on a bright, sunny day; (B) photograph taken from ground level on a cloudy day; (C) photograph taken at a distance of 8 meters from tree on a bright, sunny day; and (D) photograph taken from an elevated position (4 meters) on bright, sunny day.
Figure 2:
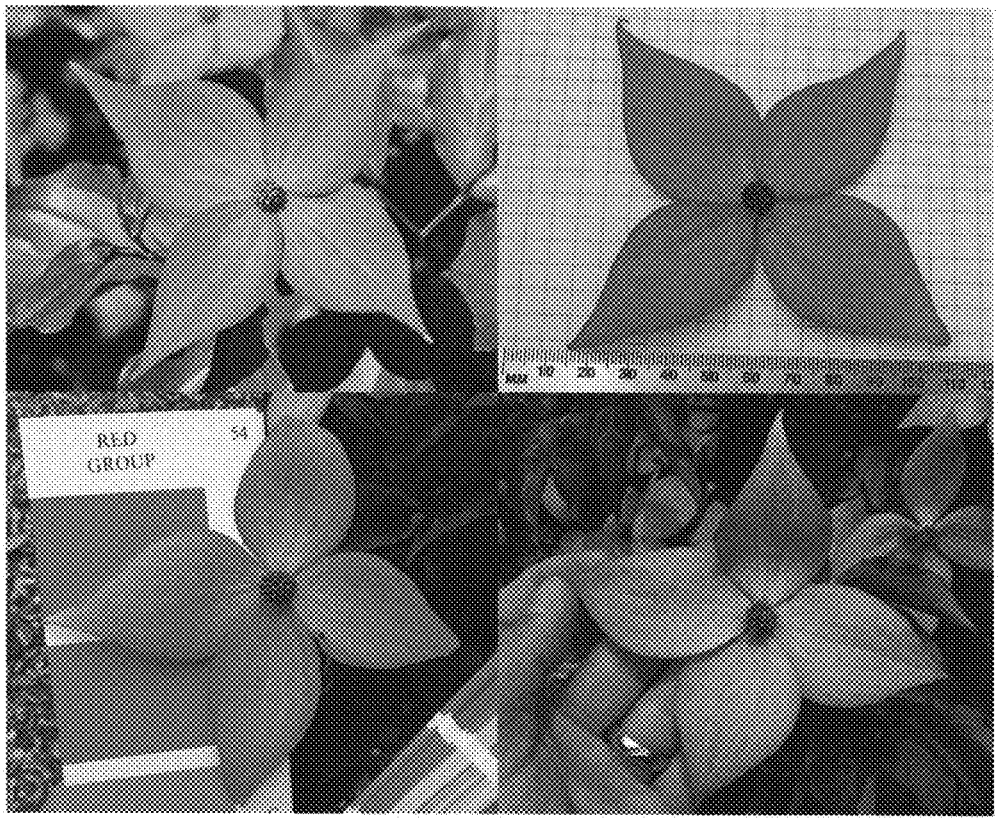
FIG. 2 shows four images representing close-up views of individual flower heads at peak ornamental display or shortly after. Note that the images show the distinctly acuminate floral bracts. From left to right top to bottom: (A) photograph taken in full sun on date of peak floral display prior to true flowers opening; (B) photograph taken out of direct sunlight on date of peak floral display; (C) photograph taken out of direct sunlight and next to R.H.S. Colour Chart card Red Group 54 for bract color comparison; and (D) photograph taken several days after peak floral display. Floral bracts fade to a lighter pink color once true flowers are open.
Figure 3:
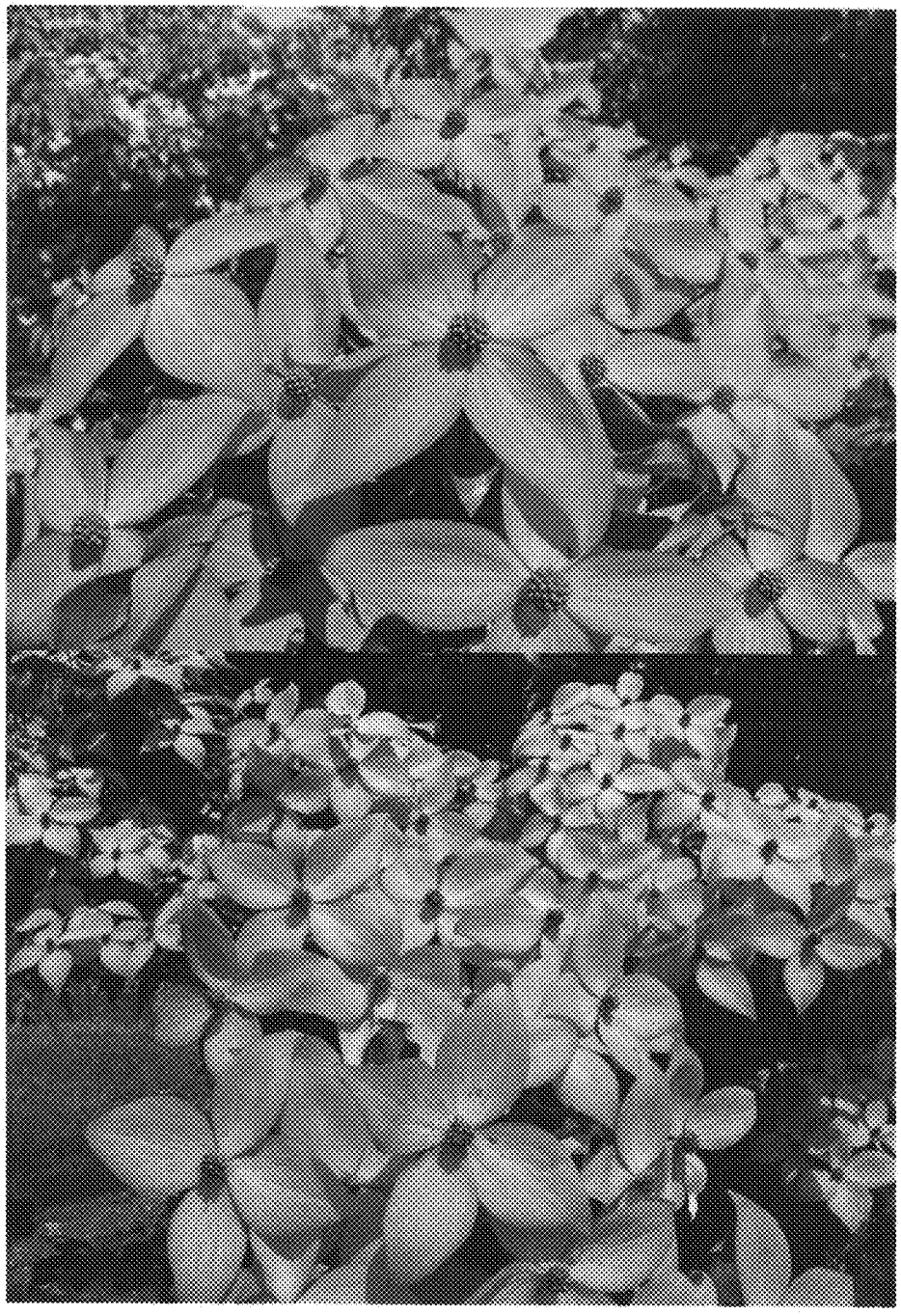
FIG. 3 shows two digital images that represent the high density of flower heads per branch, which is a defining characteristic of 'Rutpink'. The top image (A) was taken on a bright, sunny day at peak floral display. The bottom image (B) was taken on a cloudy day several days after true flowers opened. Note in the second image the floral bracts are slightly wider and the color is a lighter pink.
Figure 4:
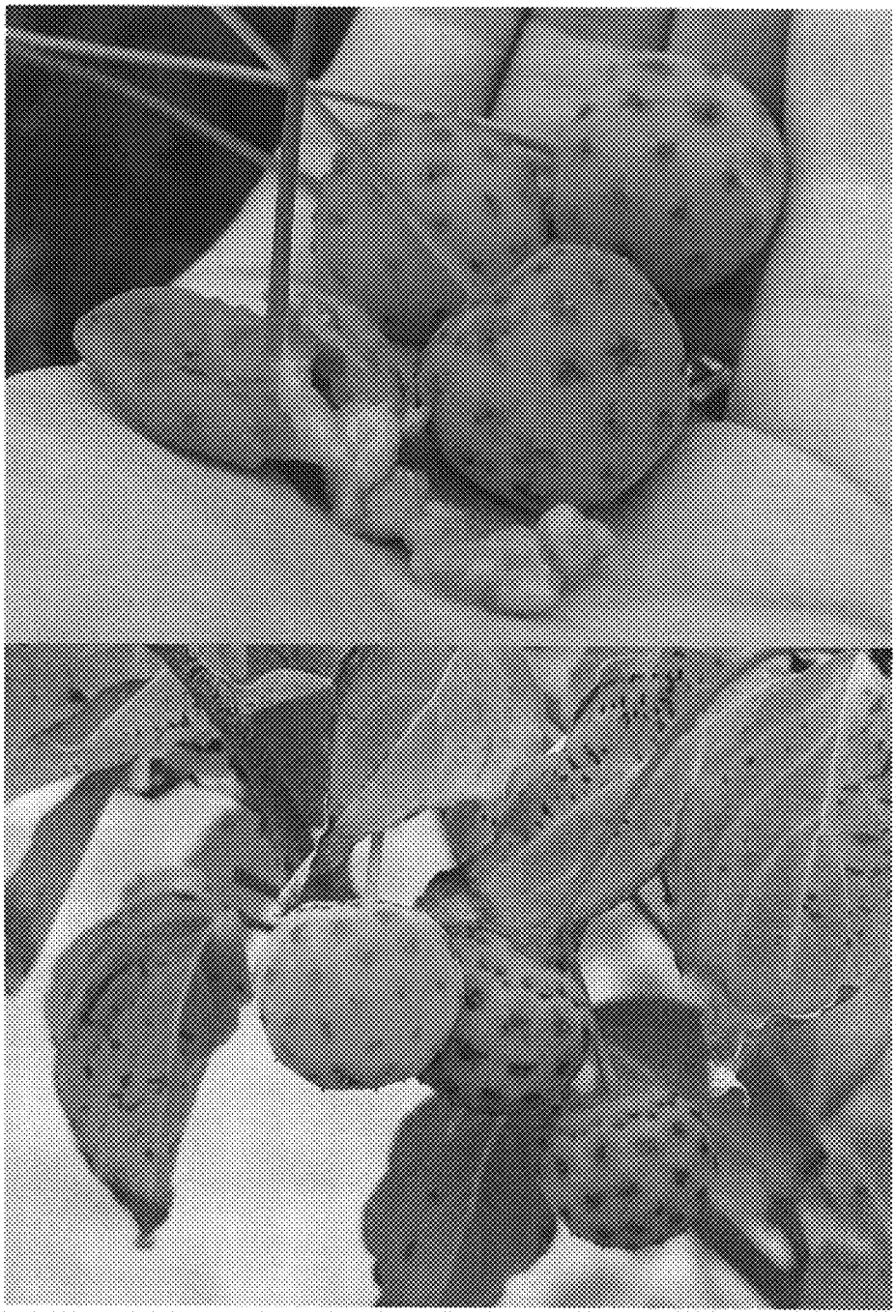
FIG. 4 shows two digital images that represent the color and shape of mature fruit, which is consistent with the species. The top image (A) shows fruit that have just reached maturity. The lower image (B) shows older fruit that are beginning to senesce (soften), as well as a typical representation of fall leaf color.

Form: Tree.

Growth habit: Dense tree branched low to ground with upright branches which form a rounded, but spreading, head. Vigorous but compact, and slightly taller than wide.

Height: 3.20 meters at 7 years.

Spread: 2.50 meters at 7 years. Plant vigor is similar to the species.

Cold hardiness: The original seedling, and five grafted propagules thereof, have suffered no visible winter injury to vegetative or floral buds during the 6 and 2 winters since 2009 and 2013, respectively, that the plants have been under test in the field at New Brunswick, N.J., in USDA Plant Hardiness Map Zone 6a (−5 degree. to −10 degree F.).

Resistance to insects and diseases: No evidence of insect problems has been observed on the original seedling, or its propagules, in the years the plants have been under test in New Jersey, Tennessee, and Oregon. An inconsequential amount of powdery mildew was observed on the original seeding plant in the year 2012 and 2014 in New Jersey and a small amount in 2014 in Tennessee on late season vigorous growth with none reported from Oregon. No evidence of susceptibility to Dogwood anthracnose or common dogwood borer has been presented.

Trunk: Circumference of the trunk at 10 cm above the soil level was 29 cm after 7 growing seasons.

Texture: Smooth, although some parts sandpaper rough due to presence of lenticels.

Color of bark on trunk and main scaffold branches: Closest to 197A and 197B Greyed Green Group. Younger stems (1 and 2 years) closest to 200 C and 200 B Brown Group. Three-year-old branches closest to 197A and 197B Greyed Green Group and sandpaper rough due to the presence of lenticels (average 15-20 per $cm^2$). Lenticels are closest to 156 B Greyed White Group. Size of lenticels is 1.0-2.0 mm long by 0.3 mm-0.4 mm wide. Lenticels are present on younger stems but are less than 1.0 mm long, same color.

Branches: Crotch angle 35-55 degrees for large, major branches, but 45-70 degrees for subsequent smaller branches.

FOLIAGE

Leaf arrangement: Opposite.

Leaf size: Lamina.

*Average length.*—96.7 mm (range 76-115; n=50).

*Average width.*—55.8 mm (range 41-76, n=50), the widest point being a little more than half-way down from the tip.

Petiole: Average length 6.4 mm (range 3-12 mm, n=50). Average diameter 1.3 mm (Range 1.1 mm-1.5 mm) n=50.

Shape: Ovate/elliptic.

Tip: Acuminate.

Base: Rounded.

Number of pairs of veins: 4 to 5.

Margin: Moderately wavy with some leaves slightly folded towards adaxial side along mid vein.

Texture: Adaxial surface is smooth. The abaxial surface is slightly fuzzy due to many minute trichomes on the blade and tufts of longer, thin hairs in clumps along the midrib and the secondary veins, especially at the junctures of the midvein and $4^{th}$ and $5^{th}$ pairs of secondary veins.

Quantity: Densely foliaged. (See FIG. 1 A-D).

Coloration: Solid.

Mature leaf color:

*Adaxial.*—Closest to 137A-B Green Group.

*Abaxial.*—Closest to 138 B Green Group. The color of the lower one third of the mid vein on the adaxial side is 59 A Red-purple group. The same color also extends to the lower one third of the 4th or 5th secondary veins closest to the petiole. The color of the mid vein on the abaxial side is 160 D Greyed Yellow group with most secondary veins 59 A Red-Purple Group.

*Petiole.*—Closest to 59 A Red Purple group.

Immature leaf color:

*Adaxial.*—Leaf surface areas closest to the veins are 144 A Yellow Green Group and in the regions between veins 187 A to 187 B Greyed Purple group. Veins are 59 A Red-Purple Group.

*Abaxial.*—Mostly 146 C Yellow-green group with some interveinal splotches of 187 A Greyed Purple Group. Petiole is closest to 59 A Red-purple group.

Autumn foliage color (mid-October), New Brunswick, New Jersey.

*Adaxial surface.*—Most leaves 137A Green Group but mottled with other colors (mostly 187A Greyed-Purple Groups, 183A Greyed-Purple Group, 53A Red Group, 46A Red Group, 43A Red Group, and 9A Yellow Group).

*Abaxial surface.*—138A Green Group. Leaf color is dependent on many environmental factors such as soil type, exposure to sun, air temperature, day length, available water and nutrients. Thus, leaf color may vary from one area to another.

INFLORESCENCE

Location where observations were made: New Brunswick, New Jersey.

Type of inflorescence: Flower head. Dense, rounded mound.

Peduncle size (late May at time of anthesis): Average length (n=50): 78.7 mm cm (range=63 mm to 110 mm). Average width (n=20): 1.4 mm (range=1.2 cm-1.7 cm).

FLORAL BRACTS

Number: Four (two opposing pairs, lower and upper). Size of floral bracts at time of floral period late May to early June.

TABLE 1

| Lower floral bract dimensions; | | |
|---|---|---|
| Lower bract Average length (mm) | n = 50 for all measurements Average Width (mm) | Involucral spread (mm) |
| 67.3 | 35.2 | 134.5 |

n = number of measurements.

TABLE 2

| Upper floral bract dimensions; | | |
|---|---|---|
| Upper bract Average length (mm) | n = 50 for all measurements Average Width (mm) | Involucral spread (mm) |
| 66.4 | 31.9 | 133.6 |

n = number of measurements.

The average length of the lower and upper bracts is very similar in size with the lower bracts being just slightly larger on average. The average width of the lower bracts is consistently larger than the upper bract. Bract length and width will vary slightly from year-to-year based on environmental conditions and flower head numbers within the tree canopy, but the relationship between the size of the upper and lower bracts and the ratio of length to width across all bracts remains consistent.

Shape: The individual floral bracts are distinctly acuminate with their apices terminating in a long, thin point. They are obtuse to rounded at their base. For most flower heads, bracts overlap their adjacent partner bract less than 10% of their total width at anthesis. Younger bracts show no overlap.

Color: At peak of floral display (approximately May 28 to June 2 in New Brunswick, N.J.) in full sun exposure:

*Adaxial*.—Closest to and in between 54 A and 54 B Red Group, most being 54 B.

*Abaxial*.—Closest to 51 C Red Group with some visible veins the color of 51 B Red group. Peduncle of flower head at peak floral display is 144 C Yellow Green group. Floral bract color lightens (closest to 55 D Red Group) after anthesis and prior to dropping of the bracts.

Flower description: Very floriferous. Single flowers arranged in compact, dense heads subtended by the large floral bracts. The average number of true flowers per flower head is 42, ranging from 38 to 46 (n=20). No observed fragrance. Flowers are not persistent. Floral display of the involucral bracts typically lasts about three weeks depending on weather conditions.

Flowering habit: Anthesis of the tiny, relatively inconspicuous true flowers generally begins around the time of peak ornamental display of the floral bracts (approximately May 28 to June 2 in New Brunswick, N.J.). The color of the floral bracts lightens after anthesis.

REPRODUCTIVE ORGANS

Stamens per flower: 4.

Filament:

*Length*.—Approximately 2.75 mm (n=4).

*Width*.—Approximately 0.28 mm (n=4).

*Color*.—155B White Group.

Anther:

*Length*.—Approximately 0.4 mm (n=4).

*Width*.—Approximately 0.81 mm (n=4).

Color: 162A Greyed-Yellow Group.

Pollen: Color of freshly dehisced pollen is approximately 158 A Yellow white group.

Style:

*Height*.—Approximately 1.5 mm (n=4).

*Width*.—Approximately 0.3 mm (n=4).

*Color*.—144 C Yellow-Green Group.

Stigma:

*Height*.—Approximately 0.25 mm (n=4).

*Width*.—Approximately 0.5 mm (n=4).

*Color*.—144 C Yellow-Green Group. All figures are based on an average of the 4 measurements.

FRUIT

Flower head with mature fruit. Fruits are 2-celled, typically 1-seeded, fleshy drupes that form a mounded, raspberry-like syncarp averaging 23.2 mm in length, 22.3 mm in width, and 21.0 mm in height (n=56). The many ovaries are enclosed in a fleshy, rounded mass typical for fruit of *Cornus kousa*. The exterior of the aggregate fruit is fairly smooth except for the dried floral parts at the tip of each individual drupe (the dried remains of the sepals and the persistent style and stigma).

Fruit color varies from green to yellow to orange to pink as the fruit matures and finally to 46A to 42C Red Group. Fruits ripen in late August and persist for around 6 weeks.

Seed:

*Color when dry*.—Closest to 165 C to 165 D Greyed Orange Group.

*Size*.—Average 6.4 mm length, 4.8 mm width, and 3.6 mm in thickness (n=40).

*Shape*.—Typical for *Cornus kousa*. Average number of seeds per fruit is 16 (n=36).

What is claimed is:

1. A new and distinct cultivar dogwood tree, substantially as herein shown and described, comprising an advanced generation seedling of *Cornus kousa* with dark-pink colored floral bracts.

* * * * *

A.

B.

C.

D.

A.

B.

C.

D.

A.

B.

A.

B.